United States Patent [19]

Cregge et al.

[11] Patent Number: 4,748,274

[45] Date of Patent: May 31, 1988

[54] 4-HYDROXY-4-(SUBSTITUTED ALKENYL)CYCLOHEXANECARBOXYLIC ACIDS

[75] Inventors: Robert J. Cregge, Zionsville; Nelsen L. Lentz, Indianapolis, both of Ind.

[73] Assignee: Merrell Dow Pharmaceuticals Inc., Cincinnati, Ohio

[21] Appl. No.: 928,759

[22] Filed: Nov. 7, 1986

[51] Int. Cl.$^4$ ................ C07C 149/26; C07C 149/273; A61K 31/215; A61K 31/19

[52] U.S. Cl. .................................... 562/507; 514/826; 560/16; 560/18; 560/125; 562/432; 564/154

[58] Field of Search ................ 562/507, 432; 560/125, 560/16, 18; 564/154

[56] References Cited

U.S. PATENT DOCUMENTS 4,622,422 11/1986 Cregge et al. ..................... 562/507

OTHER PUBLICATIONS

Noller, Chemistry of Organic Compounds, 2nd ed., W. B. Saunders Co., 1957, pp. 740–741.
Streitwieser et al., Introduction to Organic Chemistry, Macmillan Publishing Co., Inc., New York, 1976, pp. 242–243.

Primary Examiner—Donald B. Moyer
Assistant Examiner—Patricia M. Scott
Attorney, Agent, or Firm—John J. Kolano

[57] ABSTRACT

The present invention relates to compounds which are 4-hydroxy-4-alkenylcyclohexanecarboxylic acid derivatives possessing leukotriene antagonist activity. The compounds are useful in the treatment of allergic diseases, particularly in the treatment of human asthma. They are prepared by the reaction of an appropriate oxaspiro compound with a mercaptoalkanoic acid derivative.

7 Claims, No Drawings

4-HYDROXY-4-(SUBSTITUTED ALKENYL)CYCLOHEXANECARBOXYLIC ACIDS

The present invention relates to a group of compounds which are 4-hydroxy-4-(substituted alkenyl)cyclohexanecarboxylic acids and acid derivatives thereof. More particularly, the present invention relates to compounds having the following general formula:

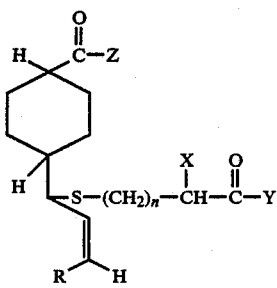

wherein n is an integer of 0 to 2; R is a straight-chain alkyl containing from 6 to 15 carbon atoms; X is hydrogen or, when n is 1 or 2, X can be —NH$_2$, Y is hydroxy, —O—(lower alkyl), —NH$_2$, —NH(lower alkyl), or —N—(lower alkyl)$_2$ or

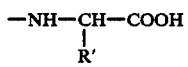

wherein R' is hydrogen, alkyl of 1 to 4 carbon atoms, or benzyl; and Z is hydroxy, —O—(lower alkyl), —NH$_2$, —NH—(lower alkyl), or —N—(lower alkyl)$_2$. Y and Z can be the same or different although they are usually the same. The lower alkyl groups referred to above contain 1 to 4 carbon atoms.

Stereoisomerism is possible with the present compounds and the chemical structure as presented above is considered as encompassing all of the possible stereoisomers and also racemic mixtures of such stereoisomers. More specifically, where the substituent in the above structure is attached to the cyclohexane ring by a single bond, two isomers are possible at each point, depending on whether the substituent is above or below the plane of the cyclohexane ring. However, in the present compounds with the substituents at the 1- and 4-positions of the cyclohexane ring, a plane of symmetry is possible so that the number of stereoisomers possible is reduced. In the case of the double bond, geometric (cis-trans) isomerism is possible, depending on the position of the R-group in the double-bonded structure relative to the remainder of the molecule. Generally, racemic mixtures can be obtained more readily than individual optical isomers so that the compounds as described and obtained in the present application should be considered as racemic mixtures unless indicated otherwise. Where absolute configuration is specified for a compound, that indicates the major optical isomer present in what is generally a mixture containing a small amount of the enantiomer.

The lower alkyl groups, as indicated above, contain 1 to 4 carbon atoms and this same definition applies to any use of the term below. Examples for such alkyl groups are methyl, ethyl, propyl and butyl. Examples of the alkyl groups for R are octyl, nonyl, decyl, undecyl, dodecyl, tridecyl, tetradecyl and pentadecyl.

The therapeutically acceptable salts of the foregoing acids, i.e., where Y and/or Z are -OH, are also included within the scope of the present invention. These basic salts would include, but would not be limited to, sodium, potassium, calcium, magnesium, triethylamine, tromethamine, dicyclohexylamine and the like as is well-known in the art. Such base salts can be obtained by standard procedures using the free acids of the present invention and the appropriate base. The preferred compounds of the present invention, however, are those wherein both Y and Z are hydroxy.

As examples of compounds of the present invention are the following:

[4(R)-[1α,4β,4(Z)]]-4-[1-[(2-carboxyethyl)thio]-2-hexadecenyl]-4-hydroxycyclohexanecarboxylic acid.

[4(R)-[4α,4β,4(Z)]]-4-[1-[(carboxymethyl)thio]-2-hexadecenyl]-4-hydroxycyclohexanecarboxylic acid.

[4(R)-[1α,4β,4(Z)]]-4-[1-[(2-carboxyethyl)thio]-2octadecenyl]-4-hydroxycyclohexanecarboxylic acid.

[4(R)-[1α,4β,4(Z)]]-4-[1-[(2-carboxyethyl)thio]-2tetradecenyl]-4-hydroxycyclohexanecarboxylic acid.

[4(R)-[1α,4β,4(Z)]]-4-[1-[(carbamoylmethyl)thio)-2-hexadecenyl]-4-hydroxycyclohexanecarboxylic acid.

[4(R)-[1α,4β,4(Z)]]-4-[1-[(3-carboxypropyl)thio]-2hexadecenyl]-4-hydroxycyclohexanecarboxylic acid.

[4(R)-[1α,4β,4(Z)]]-4-[1-(2-amino-2-carboxyethyl)-thio]-2-hexadecenyl]-4-hydroxycyclohexanecarboxylic acid.

[4(R)-[1α,4β,4(Z)]]-4-[1-[[N-carboxymethyl)carbamoylmethyl]thio]-2-hexadecenyl]-4-hydroxycyclohexanecarboxylic acid.

[4(R)-[1α,4β,4(Z)]]-4-[1-[[N-(1-carboxybutyl)caramoylmethyl]thio]-2-hexadecenyl]-4-hydroxycyclohexanecarboxylic acid.

[4(R)-1α,4β,4(Z)]]-4-[1-[[N-(1-carboxy-2-phenylethyl)carbamoylmethyl]thio)-2-hexadecenyl]-4-hydroxycyclohexanecarboxylic acid.

[4(R)-[1α,4β,4(Z)]]-4-[1-[(carbamoylmethyl)thio]-2-hexadecenyl]-4-hydroxycyclohexanecarboxamide.

[4(R)-[1α,4β,4(Z)]]-4-[1-[(N-methylcarbamoylmethyl)-thio]-2-hexadecenyl]-4-hydroxy-N-methylcyclohexanecarboxamide.

[4(R)-[1α,4β,4(Z)]]-4-[1-[(N,N-diethylcarbamoylmethyl)thio]-2-hexadecenyl]-4-hydroxy-N,N-diethylcyclohexanecarboxamide.

[4(R)-[1α,4α,4(Z)]]-4-[1-[(2-carboxyethyl)thio]-2hexadecenyl]-4-hydroxycyclohexanecarboxylic acid.

[4(R)-[1α,4α,4(Z)]]-4-[1-[(2-carboxyethyl)thio]-2-hexadecenyl]-4-hydroxycyclohexanecarboxylic acid.

[4(S)-[1α,4α,4(Z)]]-4-[1-[(2-carboxyethyl)thio]-2hexadecenyl]-4-hydroxycyclohexanecarboxylic acid.

[1α,4α,4(Z)]-(±)-4-[1-[(2-carboxyethyl)thio]-2-hexadecenyl]-4-hydroxycyclohexanecarboxylic acid.

[1α,4β,4(Z)]-(±)-4-[1-[(2-carboxymethyl)thio]-2-hexadecenyl]-4-hydroxycyclohexanecarboxylic acid.

[1α,4β,4(E)]-(±)-4-[1-[(2-carboxyethyl)thio]-2-hexadecenyl]-4-hydroxycyclohexanecarboxylic acid.

[4(S)-[1α,4β,4(E)]]-4-[1-[(carboxymethyl)thio]-2-hexadecenyl]-4-hydroxycyclohexanecarboxylic acid.

The compounds of the present invention are prepared by reacting an epoxide of the formula:

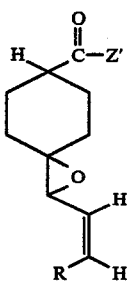

wherein R is defined as above and Z' is —O—(lower alkyl), —NH₂, —NH(lower alkyl), or —N—(lower alkyl)₂, with a mercaptoalkanoic acid derivative of the formula:

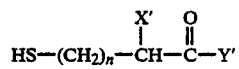

wherein n is an integer from 0 to 2; X' is hydrogen or, when n is 1 or 2, X' can be Q—NH— wherein Q is an amine-protecting group; Y' is —O—(lower alkyl), —NH₂, —NH(lower alkyl), —N—(lower alkyl)₂ or

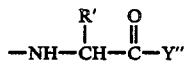

wherein R' is hydrogen, alkyl of 1 to 4 carbon atoms or benzyl and Y" is —O— (lower alkyl); in an appropriate solvent in the presence of base, optionally followed, when Y', Y" or Z' are —O—(lower alkyl), by treatment with a strong inorganic base followed by acidification with strong acid to give those compounds wherein Y, Y" or Z are —OH. Although Y' and Z' are more commonly the same in the above reactants, they do not have to be the same and this is a convenient point for introducing differences in the acid functions involved by the appropriate choice of reactants. Obviously, where one of the groups Y' and Z' in the product is an ester [i.e., —O—(lower alkyl)], this group can be further hydrolyzed by standard procedures to give the corresponding free carboxylic acid group.

Although a protecting group is not specifically necessary when X is —NH₂, the amine group can be protected by one of the standard protecting groups in amino acids. Trifluoroacetyl is a preferred group for this purpose since it would be hydrolyzed at the same time as any Y or Z ester groups to leave a free amino group. Benzyloxycarbonyl is also a useful protecting group although the conditions necessary for hydrolysis are stronger than those for a trifluoroacetyl group. However, the benzyloxycarbonyl group can also be removed by catalytic hydrogenation without affecting any ester groups present elsewhere in the molecule.

The base used in the epoxide opening process is preferably a tertiary amine such as triethylamine. The solvent used for the reaction should be one which dissolves the reactants but is inert with respect to the reaction itself. Lower alkanols are the preferred solvents and, particularly, lower alkanols which would correspond to the alcohol portion of any ester used in the reaction. Thus, methanol would be used in the case of methyl esters while ethanol would be used in the case of ethyl esters.

The subsequent saponification of the esters with a strong base followed by acidification of the resulting salt mixture to give the corresponding free acid are all standard procedures in organic chemistry so that it should not be necessary to elaborate on the reagents and reaction conditions used.

The epoxides used as the starting materials in the general process described above can be obtained from available starting materials using an appropriate series of reactions. Thus, methyl 4-hydroxybenzoate is hydrogenated using 5% rhodium on alumina as catalyst to give methyl 4-hydroxycyclohexanecarboxylate. This is then oxidized with pyridinium chlorochromate resulting in methyl 4-oxocyclohexanecarboxylate. The 2-carbon homologation of methyl 4-oxocyclohexanecarboxylate to give methyl 4-(oxoethylidene)cyclohexanecarboxylate is carried out using the method developed by A. I. Meyers. Acetaldehyde t-butylimine is metalated with lithium diisopropylamide and then treated with diethyl chlorophosphate to provide the lithioeneaminephosphonate. Addition of methyl 4-oxocyclohexanecarboxylate and subsequent acid hydrolysis gives methyl 4-(oxoethylidene)cyclohexanecarboxylate. The reduction of this oxoethylidene compound with sodium borohydride gives methyl 4-(2-hydroxyethylidene)cyclohexanecarboxylate.

The conversion of the hydroxyethylidene compound to the desired epoxide intermediate can be illustrated by the following series of reactions:

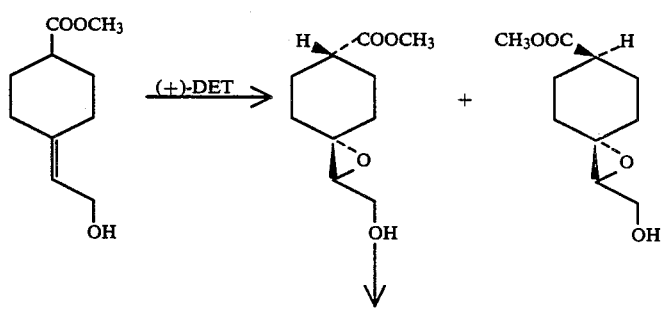

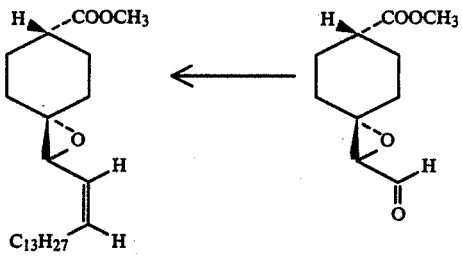

More specifically, chirality is introduced at this point in the synthetic procedure by using the known Sharpless asymmetric epoxidation technique whereby the hydroxyethylidene compound is treated, for example, with (+)-diethyl tartrate, titanium (IV) isopropoxide and t-butylhydroperoxide producing two diastereomers, methyl 2-(hydroxymethyl)-[3-(S)-cis or trans]-1-oxaspiro[2.5]octane-6-carboxylate. The cis form of the indicated compound is oxidized by means of the known Swern oxidation technique using oxalyl chloride, dimethylsulfoxide and triethylamine to produce methyl 2-formyl-[3(S)-cis]-1-oxaspiro[2.5]octane-6-carboxylate. Wittig olefination of this compound using an alkyltriphenylphosphonium bromide and potassium t-butoxide gives a methyl 2-(1-alkenyl)-[3(S)-[3α,3(Z),6α]]-1-oxaspiro[2.5]-octane-6-carboxylate. Use of (-)-diethyl tartrate in the epoxidation procedure referred to earlier provides the other two isomers of the 2-(hydroxymethyl) compound which are then reacted further as described above to give the 3(R)-isomers.

In those instances where the final product desired is an amide, such compounds can be obtained by using the appropriate reagents in the procedures described above. Alternatively, the esters of the present invention obtained as described previously can be converted to the corresponding amides by reaction with ammonia or an appropriate amine.

The specific conditions used in the processes referred to above are described in more detail in the examples below.

The compounds of the present invention are useful in the treatment of allergic diseases and, particularly, in the treatment of bronchial asthma. Thus, SRS-A (slow-reacting substance of anaphylaxis) is known as a substance which is a very important mediator in allergic bronchial asthma. Specifically, SRS-A is a substance which is synthesized and released in or near target tissues, in a sensitive allergic subject, shortly after challenge by the appropriate antigen with the human bronchus being particularly sensitive to SRS-A. Thus, a substance which would counteract the effects of SRS-A would be useful in the treatment of bronchial asthma.

More recent studies have established that SRS-A is actually a mixture of substances which can be described as peptido-leukotrienes. LTD$_4$ is one of these leukotrienes and can be considered as representative of them so that antagonism of this specific substance would provide effects similar to the antagonism of SRS-A generally. Specifically, the compounds of the present invention are useful as antagonists of LTD$_4$ so that they are useful in the treatment of allergic diseases and, particularly in the treatment of bronchial asthma. The present compounds are selective in this antagonist activity in that they are not considered as competitive against histamine or carbachol.

The activity of the compounds of the present invention can be demonstrated by the following test procedures.

Longitudinal Muscle of Guinea Pig Ileum

Male, Hartley-Duncan, guinea pigs were sacrificed by cervical dislocation. The terminal portion of the ileum was removed, rinsed, and placed in Burn's modified Tyrode's solution. The longitudinal muscle was then carefully dissected from the circular muscle of the ileum. The longitudinal muscle was cut into 1–2 cm. segments which were placed in a tissue bath containing oxygenated Burn's modified Tyrode's solution warmed to 37° C. A tension of 1.0 gram was then placed on each segment of muscle. After equilibration for 1 hour, 1 μM Indomethacin was added to each bath. After 5 minutes, each tissue segment was then exposed to a concentration of 60 nM leukotriene D$_4$. This response was then considered to be the initial maximal contraction that each segment will produce. After washing the tissue several times, over a 1 hour period, 1 μM Indomethacin was again added to each bath. After a 5 minute period the test agent or vehicle was added to the bath. After 15 minutes, a concentration-response curve was generated using cumulatively increasing concentrations of leukotriene D$_4$. The concentration-response was then compared to the initial maximum contraction. A test compound was considered active, if at concentrations up to 100 μM, it produces a significant shift to the right of the concentration-response relationship to leukotriene D$_4$. The antagonist activity was quantitated in terms of a pA$_2$ value calculated according to the method described by Arunlakshana and Schild, (Brit. J. Pharmac. Chemotherap. 14; 48, 1959).

3H-LTD$_4$ - Specific Receptor Binding in Guinea Pig Lung Membranes

Male guinea pigs were sacrificed and the lungs were removed and placed in ice cold 50 mM Tris-HCl buffer, pH 7.4. The lungs were then homogenized with a Polytron homogenizer and the homogenate was centrifuged at 1000 g for 10 minutes at 4° C. The supernatant was then centrifuged at 30,000 g for 15 minutes at 4° C. to obtain the membrane pellet. This pellet was resuspended in 50 mM Tris-HCl to provide the working suspension of lung membranes. Binding assays were then carried out in 50 mM Tris-HCl at pH 7.6 and 37° C. using incubation periods of 20–40 min. Separation of bound $^3$H-LTD$_4$ from free $^3$H-LTD$_4$ were performed by rapid vacuum filtration through Whatman GF/B glass fiber filters using ice cold Tris-HCl buffer and three 4 ml washes. Filtration and washing were completed in less than 8 seconds. The radioactivity on the filters was then measured. Specific binding of $^3$H-LTD$_4$ was defined as the binding of $^3$H-LTD$_4$ in the absence of unlabelled LTD$_4$ minus the binding of $^3$H-LTD$_4$ in the presence of $2 \times 10^{-7}$M unlabelled $LTD_4$. Specific binding of $^3H$-$LTD_4$ was 60–80% of total binding. Studies with test agents demonstrate the ability of the test compound to inhibit the specific binding of $^3H$-$LTD_4$. In these tests increasing concentrations of the agent are used to block the $^3H$-$LTD_4$ specific binding. The concentration that reduces the specific binding of $^3H$-$LTD_4$ by 50% is termed the $IC_{50}$.

The specific activity observed for some compounds of the present invention when tested by the above procedures is summarized in the table below. Variations in activity occur, however, and it appears that activity decreases with a decrease in the length of the R-alkyl groups from the tetradecylidene compounds included in the table.

| COMPOUND (EXAMPLE NO.) | G.P. ILEUM $pA_2$ ($LTD_4$) | G.P. LUNG SPECIFIC BINDING $IC_{50}$, $\mu M$ |
| --- | --- | --- |
| 10D | 9.8 | — |
| 10H | 9.61 | 8.7 |
| 10F | 9.42 | — |
| 11 | 7.87 | — |
| 10J | 8.26 | 7.1 |
| 10L | 8.57 | 8.0 |

In Vivo Biological Activity

Compounds of the present invention were also tested for in vivo leukotriene $D_4$ antagonist activity in anesthetized guinea pigs using a modified Konzett-Rössler preparation. Specifically, the guinea pigs were anesthetized with sodium pentobarbital and surgically prepared for artificial ventilation by a constant volume respirator. The inflation pressure produced by the respirator was measured for each inflation of the guinea pigs' lungs. Increases in inflation pressure above baseline are indicative of bronchoconstriction. After establishing a baseline inflation pressure, bronchoconstriction was induced by an intravenous challenge with 50 or 100 ng/kg leukotriene $D_4$. This response was considered the initial response. After the inflation pressure returned to baseline, the guinea pig was treated with the desired dosage of test compound or vehicle, given intravenously (i.v.) or intraduodenally (i.d.), and rechallenged with leukotriene D at one minute [following i.v. administration] or 5 and 20 minutes [following i.d. administration]. This response was then compared to the initial response and the % inhibition of the response was determined. The results can be summarized as follows, with the inhibition values given for administration by the i.d. route being the greater of the two results obtained.

| COMPOUND (EXAMPLE NO.) | DOSE | ROUTE | PERCENT INHIBITION |
| --- | --- | --- | --- |
| 10F | 0.0002 mg/kg | i.v. | 38 |
| 10F | 0.002 mg/kg | i.v. | 52 |
| 10F | 0.02 mg/kg | i.v. | 94 |
| 10F | 0.1 mg/kg | i.d. | 74 |
| 10F | 0.2 mg/kg | i.d. | 93 |
| 10J | 0.5 mg/kg | i.d. | 48 |
| 10J | 1.0 mg/kg | i.d. | 53 |
| 10I | 0.05 mg/kg | i.v. | 19 |
| 10L | 0.5 mg/kg | i.v. | 74 |
| 10L | 1.0 mg/kg | i.d. | 25 |

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection. The compounds are most preferably administered in oral dosage forms.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maizestarch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs. Procedures for the preparation of compositions as discussed above are described in standard texts, such as *Remington's Pharmaceutical Sciences*, Mack Publishing Company, Easton, Pennsylvania.

The compounds of the present invention or pharmaceutical compositions thereof may be administered to human asthmatic patients at dosages in the range from about 0.1 to about 40 mg/kg. Single oral doses of approximately 0.1–1000 mg of active ingredient and multiple oral doses totaling up to about 4000 mg/day of active ingredient can be used. When administered by inhalation, lower doses are generally given, i.e., on the order of about 0.1 of the normal dosage for the particular compound in question. These values are illustrative only, however, and the physician of course will ultimately determine the dosage most suitable for a particular patient on the basis of factors such as age, weight, diagnosis, severity of the symptoms and the particular agent to be administered.

The following examples are presented to illustrate the present invention but they should not be construed as limiting it in any way.

EXAMPLE 1

A Parr bottle was charged with 150 ml of methanol and 25 g of methyl 4-hydroxybenzoate was added, then the bottle was flushed with nitrogen, 2.5 g of 5% rhodium on alumina was added and the reaction mixture was pressurized under hydrogen at 3.74 atmospheres for 18 hours with constant shaking. The reaction was then flushed with nitrogen and filtered through diatomaceous earth to remove the catalyst. The diatomaceous earth was rinsed with methanol, being careful not to filter the catalyst to dryness. The filtrates were combined and the methanol was removed under reduced pressure with very gentle heat (ca. 40° C.). The residue of product and alumina was taken up in 200 ml of ether to which 3 g of anhydrous potassium carbonate was added. The precipitated alumina and potassium carbonate were removed by filtration through diatomaceous earth. This was rinsed with ether, the filtrates were combined and the solvent was removed under reduced pressure to yield the crude product. This was bulb-to-bulb distilled on Kugelrohr apparatus at 80°–100° C./ca. 1 mm to yield 25.0 g (98%) of methyl 4-hydroxycyclohexanecarboxylate. $^1$H NMR (CDCl$_3$, 60 MHz) δ 3.85 (s, 1 H); 3.65 (s, 3 H); 2.50–1.20 (m, 10 H).

EXAMPLE 2

To 400 ml of dry dichloromethane was added 24 g of oven dried Celite, 11.4 g of sodium acetate and 90.5 g of pyridinium chlorochromate with stirring. An additional 350 ml of methylene chloride was added followed by the addition of 44.5 of of methyl 4-hydroxycyclohexanecarboxylate in 40 ml of dichloromethane with a syringe. After 3.5 hours, 800 ml of ether was added with stirring and the mixture was suction filtered through 250 g of silica gel and the solid was washed four times with ether. The combined filtrates were concentrated to a green oil which was taken up in 150 ml of ether and again suction filtered through 50 g of silica gel and the silica gel was rinsed with ether. The combined filtrates were concentrated to a clear oil which was Kugelrohr distilled at 65°–85° C./ca. 1 mm to yield 42.6 g (97.5%) of methyl 4-oxocyclohexanecarboxylate. $^1$H MNR (CDCl$_3$, 60 MHz) δ 3.70 (s, 3H); 2.9–1.8 (9 H).

EXAMPLE 3

A mixture of 729 ml of dry tetrahydrofuran and 76.4 ml of dry diisopropylamine was cooled to 3° C. with an ice-water bath. Then 340.6 ml of n-butyllithium in hexane was added dropwise over 45 minutes, followed by an additional 15 minutes of stirring. The solution was then cooled to −75° C. and 26.9 g of acetaldehyde t-butylimine was added dropwise with a syringe over 20 minutes, followed by an additional 30 minutes of stirring. With the temperature still at −75° C., 47.0 g of diethyl chlorophosphate was added with a dropping funnel over 1 hour. The reaction was allowed to stir for an additional hour at −75° C., warmed to −11° C. over 2 hours and cooled again to −75° C. Then, 28.4 g of methyl 4-oxocyclohexanecarboxylate in 50 ml of tetrahydrofuran was added with a dropping funnel over 1 hour. The reaction was allowed to warm to room temperature overnight. It was then poured into a mixture of 49.0 g of oxalic acid in 1.8 l of water and 1.8 l of toluene. This was stirred vigorously for 24 hours and the aqueous layer was then separated and extracted with ether (2×500 ml). The combined toluene and ether extracts were washed with aqueous 5% oxalic acid (2×500 ml), 500 ml of saturated sodium bicarbonate and 500 ml of saturated sodium chloride. The organic layer was then dried over anhydrous potassium carbonate, filtered and concentrated under vacuum. The resulting oil was purified on the Prep LC (25% ethyl acetate/hexane, 300 ml/min., 2 min./cm, 2 columns, R$_t$=7.5 min.) to give 18.5 g of methyl 4-(oxoethylidene)cyclohexanecarboxylate. $^1$H NMR (CDCl$_3$, 60 MHz) δ 10.05 (d, 1 H); 5.85 (d, 1 H); 3.70 (s, 3 H); 2.8–1.5 (9 H).

EXAMPLE 4

A solution was prepared from 77 ml of methanol and 13.0 g of methyl 4-(oxoethylidene)cyclohexanecarboxylate and cooled to 3° C. with an ice-water bath. With vigorous stirring, 3.1 g of sodium borohydride was added in portions over 30 minutes. The reaction was allowed to stir for an additional hour at 3° C. before glacial acetic acid (1 ml) was added to quench the reaction and the methanol was removed under reduced pressure. The residue was taken up in 200 ml of dichloromethane and partitioned with 400 ml of water. The organic layer was separated and washed with 200 ml of saturated sodium chloride, dried over anhydrous sodium sulfate, filtered and concentrated under vacuum. The resulting oil was purified on the Prep LC (30% ethyl acetate/hexane, 250 ml/min., 2 min./cm, 2 columns, R$_t$=13 min.) to give 11.5 g of fairly pure product. Bulb-to-bulb distillation on the Kugelrohr at 150°–160° C./0.8 mm yielded 9.03 g (69%) of methyl 4-(2-hydroxyethylidene)cyclohexanecarboxylate. $^1$H NMR (CDCl$_3$ 60 MHz) δ 5.40 (t, 1 H); 4.10 (d, 2 H); 3.70 (s, 3 H); 2.9–1.3 (10 H).

EXAMPLE 5

To 300 ml of dry dichloromethane cooled to −25° C. to −30° C. with a dry ice/acetone bath was added, with stirring, 12.9 ml of titanium (IV) isopropoxide and a solution of 8.9 ml of (+)-diethyl tartrate in 10 ml of dichloromethane successively with a syringe. After 10 minutes, 8.0 g of methyl 4-(2-hydroxyethylidene)cyclohexanecarboxylate in 20 ml of dichloromethane was added to the reaction followed by a 20 ml dichloromethane rinse of the flask and syringe. Then, 18.4 ml of 4.7 M t-butylhydroperoxide in toluene was added immediately. The reaction flask was then transferred to a freezer and allowed to sit undisturbed at −20° C. for 24 hours. The reaction was then suction filtered through silica gel which was washed with 500 ml of 25% ethyl acetate/dichloromethane. The combined filtrates were concentrated under vacuum to give a yellow oil. Thin layer chromatography (20% ethyl acetate/hexane) of the crude mixture indicated that the syn and anti diastereomers were separable by chromatography with R$_f$ syn=0.14 and R$_f$ anti=0.17. These were separated on the Prep LC (10% isopropanol/hexane, 250 ml/min., 2 min./cm, 2 columns, R$_t$ anti=16 min., R$_t$ syn=23 min.) to yield 2.7 g of anti epoxide and 2.5 g of syn epoxide as oils. The syn epoxide was recrystallized twice from 3% ether/pentane to give 0.41 g of methyl 2-(hydroxymethyl)-[3(S)-cis-1-oxaspiro[2.5]- octane-6-carboxylate as long, flat, white crystals melting at 67°–68° C.; $[\alpha]_D^{20}$ −13.3° (c 1.15, chloroform); %ee= >95%. The anti epoxide was recrystallized twice from 30% ether/pentane to give 0.57 g of long, flat, white crystals melting at 31°–33° C.; $[\alpha]_D^{20}$ −10.6° (c 1.22, chloroform); %ee=80%. $^1$H NMR for the syn epoxide (CDCl$_3$, 300 MHz) δ 3.80 (m, 2 H); 3.70 (s, 3 H); 3.10 (dd, 1 H); 2.00–1.40 (9 H).

EXAMPLE 6

A mixture was prepared from 27 ml of dry dichloromethane and 0.20 ml of oxalyl chloride. The mixture was cooled to −75° C. and 0.35 ml of dimethyl sulfoxide was added dropwise over 5 minutes with stirring. After an additional 10 minutes, 381 mg of methyl 2-(hydroxymethyl)-[3(S)-cis]-1-oxaspiro[2.5]octane-6-carboxylate in 3 ml of dichloromethane was added dropwise to the reaction. After 20 minutes of stirring, 1.45 ml of triethylamine was added dropwise over 5 minutes. The reaction was then allowed to warm to room temperature over 45 minutes and the solvent was removed under reduced pressure. The white solid residue was taken up in 50 ml of ether and filtered through a sintered glass funnel. The filtrate was concentrated under vacuum to yield a yellow oil. This crude material was purified on the Prep LC (20% ethyl acetate/hexane, 250 ml/min., 2 min./cm, 1 column, $R_t$=4.75 min.) to yield 355.5 mg of methyl 2-formyl-[3(S)-cis]-1-oxaspiro[2.5]octane-6-carboxylate as an oil. $[\alpha]_D^{20}$+132.0° (c 0.71, chloroform). $^1$H NMR (CDCl$_3$, 300 MHz) δ 9.50 (d, 1 H); 3.70 (s, 3H); 3.20 (d, 1H); 2.60–1.30 (9 H).

EXAMPLE 7

To 20 ml of dry tetrahydrofuran was added 1.80 g of n-tetradecyltriphenylphosphonium bromide with stirring. Then, 6.4 ml of 0.5 M potassium t-butoxide in tetrahydrofuran was added dropwise causing the solution to turn orange. After 5 minutes, 342 mg of methyl 2-formyl-[3(S)-cis]-1-oxaspiro[2.5]octane-6-carboxylate in 3 ml of tetrahydrofuran was added dropwise to the reaction, turning the solution to pale yellow. Six additional 0.5 ml aliquots of the potassium t-butoxide solution were added at 10 minute intervals, driving the reaction to completion. Water, 5 ml, was added and the reaction mixture was poured into 200 ml of ether. The mixture was washed with saturated sodium chloride (2×100 ml) and concentrated under vacuum to 100 ml. Then, 900 ml of hexane was added and the cloudy solution was suction filtered through silica gel and the silica gel was washed with 500 ml 10% ether/hexane. The combined filtrates were concentrated under vacuum to yield a yellow oil which was purified on the Prep LC (5% ethyl acetate/hexane, 250 ml/min., 2 min./cm, 1 column, $R_t$=5 min.) to yield 527 mg of methyl 2-(1-pentadecenyl)-[3(S)-[3α,3(Z),6α]]-1-oxaspiro2.5]octane-6-carboxylate as an oil. $[\alpha]_D^{20}$+25.7° (c 0.92, chloroform). $^1$H NMR (CDCl$_3$, 300 MHz) δ 5.75 (m, 1 H); 5.25 (t, 1 H); 3.70 (s, 3 H); 3.45 (d, 1 H); 2.45–1.20 (34 H).

The procedure of Example 5 was repeated using (−)-diethyl tartrate to give the other two spiro compounds and these compounds together with the anti-compound obtained in Example 5, were each reacted according to the procedures described in Example 6 and Example 7 above. In addition, the procedure of Example 7 above was also repeated using octyltriphenylphosphonium bromide in place of the tetradecyltriphenylphosphonium bromide. The products obtained in this way were as follows:

Methyl 2-(1-pentadecenyl)-[3(S)-[3β,3(Z),6α]]-1-oxaspiro[2.5]octane-6-carboxylate.
Methyl 2-(1-pentadecenyl)-[3(R)-[3α,3(Z),6α]]-1-oxaspiro[2.5)octane-6-carboxylate.
Methyl 2-(1-pentadecenyl)-[3(R)-[3β,3(Z),6α]]-1-oxaspiro[2.5]octane-6-carboxylate.
Methyl 2-(1-nonenyl)-[3(S)-[3α,3(Z),6α]]-1-oxaspiro[2.5]octane-6-carboxylate.

EXAMPLE 8

To a mixture of 227 mg of methyl 2-(1-pentadecenyl)-[3(S)-[3α,3(Z),6α]]-1-oxaspiro[2.5]octane-6-carboxylate in 2.7 ml of methanol was added, with stirring, 0.28 ml of triethylamine, followed by 0.20 ml of methyl 3-mercaptopropionate. After 24 hours, the methanol was removed under reduced pressure and the oil was taken up in 100 ml of ether. This was then washed with 50 ml 0.5 N hydrochloric acid, 50 ml saturated sodium chloride, then dried over anhydrous sodium sulfate, and filtered and concentrated under vacuum to yield a yellow oil. This was purified on the Prep LC (10% ethyl acetate/hexane, 250 ml/min., 2 min./cm, 1 column, $R_t$=22 min.) to yield 278.4 mg of methyl [4(R)-[1α,4α,4(Z)]]-4-hydroxy-4-[1-[(2-carbomethoxyethyl)thio]-2-hexadecenyl]cyclohexanecarboxylate as an oil. $[\alpha]_D^{20}$+33.5° (c 0.88, chloroform). $^1$H NMR (CDCl$_3$, 300 MHz) δ 5.60 (m, 1 H); 5.4 (t, 1 H); 3.70 (s, 3 H); 3.65 (s, 3 H); 3.60 (d, 1 H); 2.75 (m, 2 H); 2.60 (m, 2 H); 2.20–1.20 (34 H); 0.89 (t, 3 H).

EXAMPLE 9

A solution of methyl [4(R)-[1α,4α,4(Z)]]-4-hydroxy-4-[1-[(2-carbomethoxyethyl)thio]-2-hexadecenyl]cyclohexanecarboxylate was dissolved in 4.0 ml of absolute ethanol. Then, 340 mg of potassium hydroxide pellets dissolved in 3.3 ml of water was added to the cloudy solution with stirring. After 4.5 hours, the clear solution was diluted with 75 ml of water. The aqueous mixture was washed with 75 ml of ether and then acidified with 15 ml of 0.5 N hydrochloric acid. The aqueous mixture was then extracted with ethyl acetate (3×150 ml). The combined organic extracts were dried over anhydrous sodium sulfate, filtered and concentrated under vacuum to yield a dirty white solid. This was recrystallized from 10% ether/hexane to yield 157 mg (64%) of [4(R)-[1α,4α,4(Z)]]-4-[1-[(2-carboxyethyl)thio]-2-hexadecenyl]-4-hydroxycyclohexanecarboxylic acid as a clean white powder melting at 121°–123° C.; $[\alpha]_D^{20}$+32.0° (c 0.95, chloroform). $^1$H NMR (CDCl$_3$, 300 MHz) δ 5.62 (m, 1 H); 5.40 (t, 1 H); 3.62 (d, 1 H); 2.74 (m, 2 H); 2.62 (m, 2 H); 2.25–1.20 (34 H); 0.89 (t, 3 H). This compound has the following structural formula:

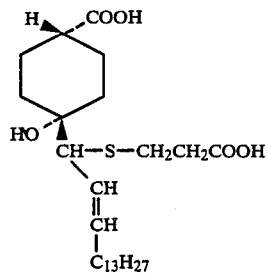

EXAMPLES 10A–10M

When the appropriate oxaspiro and mercapto compounds were reacted according to the procedure described in Example 8 and the resulting esters were saponified as described in Example 9, the following compounds were obtained:

A. [4(S)-1α,4α,4(Z)]]-4-[1-[(2-carboxyethyl)thio]-2hexadecenyl]-4-hydroxycyclohexanecarboxylic acid melting at 122°–123° C.; $[\alpha]_D^{20}$−38.1° (c 0.89, chloroform). $^1$H NMR (CDCl$_3$, 300 MHz) δ 5.61 (m, 1 H); 5.39 (t, 1 H); 3.62 (d, 1 H); 2.68 (m, 4 H); 2.23–1.22 (33 H); 0.88 (t, 3 H).

B. 4(R)-1α,4α,4(Z)]]-4-[1-[(carboxymethyl)thio]-2-hexadecenyl]-4-hydroxycyclohexanecarboxylic acid; $[\alpha]_D^{20}$+23.9° (c 0.66, chloroform). $^1$H NMR (CDCl$_3$, 300 MHz) δ 5.69 (m, 1 H); 5.39 (t, 1 H); 3.82 (d, 1 H); 3.21 (m, 2 H); 2.30–1.20 (33 H); 0.88 (t, 3 H).

C. [4(S)-[1α,4α,4(Z)]]-4-[1-[(carboxymethyl)thio]-2hexadecenyl]-4-hydroxycyclohexanecarboxylic acid; $[\alpha]_D^{20} -11.5°$ (c 1.42, chloroform). $^1$H NMR (CDCl$_3$, 300 MHz) δ 5.66 (m, 1 H); 5.37 (m, 1 H); 3.82 (d, 1 H); 3.22 (m, 2 H); 2.10–1.12 (33 H); 0.88 (t, 3 H).

D. [4(R)-[1α,4β,4(Z)]]-4-[1-[(carboxymethyl)thio]-2-hexadecenyl]-4-hydroxycyclohexanecarboxylic acid; $[\alpha]_D^{20} +3.3°$ (c 0.73, chloroform). $^1$H NMR (CDCl$_3$, 300 MHz) δ 5.75 (m, 1 H); 5.44 (m, 1 H); 4.26 (d, 1 H); 3.20 (m, 2 H); 2.40–1.18 (33 H); 0.88 (t, 3 H).

E. [4(S)-[1α,4β,4(Z)]]-4-1-[(carboxymethyl)thio]-2hexadecenyl]-4-hydroxycyclohexanecarboxylic; $[\alpha]_D^{20} -11.8°$ (c 0.97, chloroform). $^1$H NMR (CDCl$_3$, 300 MHz) δ 5.72(m, 1 H); 5.49 (m, 1 H); 4.26 (d, 1 H); 3.16 (m, 2 H); 2.50–1.17 (33 H); 0.88 (t, 3 H).

F. [4(R)-[1α,4β,4(Z)]]-4-1-(2-carboxyethyl)thio]-2hexadecenyl]-4-hydroxycyclohexanecarboxylic acid; $[\alpha]_D^{20} +34.8°$ (c 0.81, chloroform). $^1$H NMR (CDCl$_3$, 300 MHz) δ 5.63 (m, 1 H); 5.41 (t, 1 H); 3.75 (d, 1 H); 2.67 (m, 5 H); 2.09–1.26 (33 H); 0.88 (t, 3 H).

G. [4(S)-[1α,4β,4(Z)]]-4-[1-[(2-carboxyethyl)thio]-2hexadecenyl]-4-hydroxycyclohexanecarboxylic acid; $[\alpha]_D^{20} -41.4°$ (c 1.26, chloroform). $^1$H NMR (CDCl$_3$, 300 MHz) δ 5.63 (m, 1 H); 5.42 (t, 3 H); 3.76 (d, 1 H); 2.67 (m, 5 H); 2.09–1.22 (33 H); 0.88 (t, 3 H).

H. [1α,4β,4(Z)]-4-[1-[(2-CarbOxyethyl)thio]-2-hexadecenyl]-4-hydroxycyclohexanecarboxylic acid, melting at 77°–78° C. $^1$H NMR (CDCl$_3$, 300 MHz) δ 5.63 (m, 1 H); 5.41 (t, 1 H); 3.76 (d, 1 H); 2.68 (m, 5 H); 2.11–1.26 (33 H); 0.88 (t, 3 H).

I. [1α,4α,4(Z)]-4-[1-[(3-carboxypropyl)thio]-2-hexadecenyl]-4-hydroxycyclohexanecarboxylic acid, melting at 71°–72° C. $^1$H NMR (CDCl$_3$, 300 MHz) δ 5.61 (m, 1 H); 5.36 (t, 1 H); 3.59 (d, 1 H); 2.49 (m, 4 H); 2.25–1.20 (35 H); 0.88 (t, 3 H).

J. [1α,4β,4(Z)]-4-[1-[(3-carboxypropyl)thio]-2-hexadecenyl]-4-hydroxycyclohexanecarboxylic acid. $^1$H NMR (CDCl$_3$, 300 MHz) δ 5.61 (m, 1 H); 5.41 (t, 1 H); 3.69 (d, 1 H); 2.49 (m, 4 H); 2.10–1.22 (35 H); 0.88 (t, 3 H).

K. [1α,4α,4(Z)]-4-[1-[[3-[(carboxymethyl)amino]-3-oxopropyl]thio]-2-hexadecenyl]-4-hydroxycyclohexanecarboxylic acid. $^1$H NMR (CDCl$_3$, 300 MHz) δ 6.85 (m, 1 H); 5.57 (m, 1 H); 5.39 (t, 1 H); 4.27 (m, 1 H); 4.00 (m, 1 H); 3.60 (d, 1 H); 2.90–1.20 (37 H); 0.89 (t, 3 H).

L. [1α,4β,4(Z)]-4-[1-[[3-[(carboxymethyl)amino]-3oxopropyl]thio]-2-hexadecenyl]-4-hydroxycyclohexanecarboxylic acid, melting at about 81.5°–82.5° C. $^1$H NMR (CDCl$_3$, 300 MHz) δ 6.80 (s, 1 H); 5.63 (m, 1 H); 5.42 (t, 1 H); 4.08 (d, 2 H); 3.70 (d, 1 H); 2.85–2.40 (m, 4 H); 2.10–1.20 (33 H); 0.89 (t, 3 H).

M. [4(R)-[1α,4β,4(Z)]]-4-[1-(3-amino-3-oxopropyl)-thio]-2-hexadecenyl]-4-hydroxycyclohexanecarboxylic acid, melting at 108°–109° C.; $[\alpha]_D^{20} +48.3°$ (c 0.86, chloroform). $^1$H NMR (CDCl$_3$, 300 MHz) δ 6.02 (s, 1 H); 5.72 (s, 1 H); 5.60 (m, 1 H); 5.45 (t, 1 H); 3.72 (d, 1 H); 2.77 (m, 2H); 2.58 (m, 3 H); 2.15–1.20 (33 H); 0.89 (t, 3 H).

N. 4(R)-[1α,4β,4(Z)]]-4-[1-[(2-carboxyethyl)thio]-2decenyl]-4-hydroxycyclohexanecarboxylic acid.

EXAMPLE 11

A flask was charged with 315 ml of cyclohexane and flushed with nitrogen. Methyl 2-(1-pentadecenyl)-[3(S)-[3α,3(Z),8α]-1-oxaspiro[2.5]octane-6-carboxylate (397 mg) and 241 mg of diphenyl disulfide was added with stirring and the stirred solution was cooled with an ice-water bath. A sunlamp was focused down into the reaction mixture which was then illuminated for 3.6 hours. The solvent was removed under vacuum and the residue filtered through silica gel with hexane to remove diphenyl disulfide. This was followed by an ether rinse to give a solution of the crude olefin mixture. The ether was removed under vacuum to yield a yellow oil (cis/trans=1:4) which was purified on the Prep LC (15% ether/hexane, 2 column, R$_t$=8 min.) to give 120 mg of methyl 2-[(1-pentadecenyl)-[3α,(E),6β]]1-1-oxaspiro[2.5]octane-6-carboxylate as an oil. $^1$H NMR (CDCl$_3$, 300 MHz) δ 5.90 (m, 1 H); 5.33 (m, 1 H; J$_{a,b}$=15.1 Hz); 3.68 (s, 3 H); 3.18 (d, 1 H); 2.43 (m, 1 H); 2.10–1.20 (32 H); 0.89 (t, 3 H).

The product obtained above was added to 1 ml of methanol in a 5 ml round bottom flask. With stirring, 0.08 ml of triethylamine was added, followed by 0.04 ml of methyl 3-mercaptopropionate. After 2 days, the solvent was removed and the crude oil was flash chromatographed (5% ethyl acetate/hexane) to give 58.3 mg (84%) of methyl [1α,4β,4(E)]-4-hydroxy-4-[1-[(3-methoxy-3-oxopropyl)thio-2-hexadecenyl]-cyclohexanecarboxylate as a clear oil. $^1$H NMR (CDCl$_3$, 300 MHz) δ 5.45 (m, 2 H); 3.69 (s, 3 H); 3.67 (s, 3 H); 3.30 (d, 2 H); 2.80–2.20 (m, 5 H); 2.05–1.20 (33 H); 0.89 (t, 3 H).

When the above ester was hydrolyzed with base according to the procedure described in Example 9, the product obtained was [1α,4β,4(E)]-4-[1-[(2-carboxyethyl)thio-2hexadecenyl]-4-hydroxycyclohexanecarboxylic acid. $^1$H NMR (CDCl$_3$, 300 MHz) δ 5.53 (m, 2 H, J$_{a,b}$ trans=15.8 Hz); 3.37 (d, 1 H); 2.65 (m, 4 H); 2.15–1.20 (33 H); 0.88 (t, 3 H).

What is claimed is:

1. A compound of the formula:

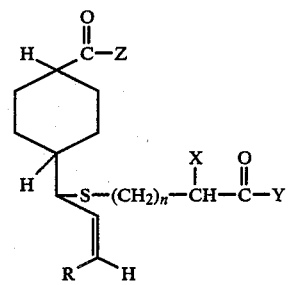

wherein n is an integer from 0 to 2; R is straight-chain alkyl containing from 6 to 15 carbon atoms; X is hydrogen or, when n is 1 or 2, X can be —NH$_2$; Y is hydroxy, —O—(lower alkyl), —NH$_2$, —NH(lower alkyl), —N—(lower alkyl)$_2$ or

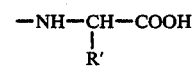

wherein R' is hydrogen, alkyl of 1 to 4 carbon atoms, or benzyl; and Z is hydroxy, —O—(lower alkyl), —NH$_2$, —NH—(lower alkyl), or —N—(lower alkyl)$_2$.

2. A compound according to claim 1 which has the formula:

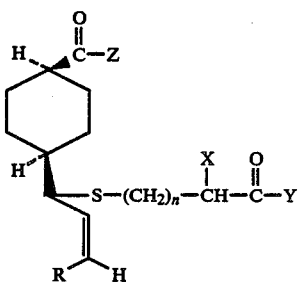

wherein n is an integer from 0 to 2; R is straight-chain alkyl containing from 6 to 15 carbon atoms; X is hydrogen or, when n is 1 or 2, X can be —NH₂; Y is hydroxy, —O— (lower alkyl), —NH₂, —NH(lower alkyl), —N—(lower alkyl)₂ or

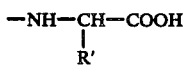

wherein R' is hydrogen, alkyl of 1 to 4 carbon atoms, or benzyl; and Z is hydroxy, —O—(lower alkyl), —NH₂, —NH—(lower alkyl), or —N—(lower alkyl)₂.

3. A compound according to claim 1 which has the formula:

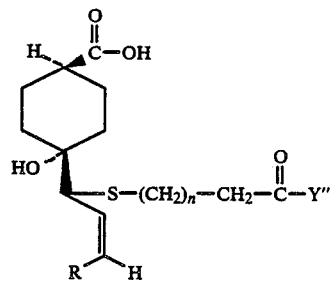

wherein n is an integer from 0 to 2; R is straight-chain alkyl containing from 6 to 15 carbon atoms; Y" is hydroxy, —NH₂, —NH(lower alkyl), —N—(lower alkyl)₂ or

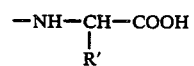

wherein R' is hydrogen, alkyl of 1 to 4 carbon atoms, or benzyl.

4. A compound according to claim 1 which is [4(R)-[1α,4β,4(Z)]]-4-[1-[(carboxymethyl)thio]-2-hexadecenyl]-4hydroxycyclohexanecarboxylic acid.

5. A compound according to claim 1 which is [1α,4β,4(Z)]-4-1-(2-carboxyethyl)thio]-2-hexadecenyl]-4-hydroxycyclohexanecarboxylic acid.

6. A compound according to claim 1 which is [4(R)-[1α,4β,4(Z)]]-4-[1-[(2-carboxyethyl)thio]-2-hexadecenyl]-4hydroxycyclohexanecarboxylic acid.

7. A compound according to claim 1 which is [1α,4β,4(Z)]]-4-[1-[(3-carboxypropyl)thio]-2-hexadecenyl]-4-hydroxycyclohexanecarboxylic acid.

* * * * *